(12) United States Patent
Hattori et al.

(10) Patent No.: US 12,329,911 B2
(45) Date of Patent: Jun. 17, 2025

(54) HUMIDIFIER

(71) Applicant: Murata Manufacturing Co., Ltd., Kyoto (JP)

(72) Inventors: Atsushi Hattori, Kyoto (JP); Ken Shin, Kyoto (JP); Yuzo Higashiyama, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 457 days.

(21) Appl. No.: 17/938,498

(22) Filed: Oct. 6, 2022

(65) Prior Publication Data

US 2023/0030885 A1 Feb. 2, 2023

Related U.S. Application Data

(63) Continuation of application No. PCT/JP2021/013010, filed on Mar. 26, 2021.

(30) Foreign Application Priority Data

Apr. 8, 2020 (JP) .................................. 2020-069629

(51) Int. Cl.
*A61M 16/16* (2006.01)
*F24F 6/04* (2006.01)

(52) U.S. Cl.
CPC ............... *A61M 16/16* (2013.01); *F24F 6/04* (2013.01)

(58) Field of Classification Search
CPC ....... A61M 16/16; F24F 6/04; F24F 2006/008
USPC ..................................................... 261/119.1
See application file for complete search history.

(56) References Cited

U.S. PATENT DOCUMENTS

| 5,598,837 | A | * | 2/1997 | Sirianne, Jr. | .......... A61M 16/16 261/119.1 |
| 6,398,197 | B1 | | 6/2002 | Dickinson et al. | |
| 6,827,340 | B2 | * | 12/2004 | Austin | ................ A61M 16/109 261/119.1 |

(Continued)

FOREIGN PATENT DOCUMENTS

| DE | 10226160 A1 | 1/2004 |
| EP | 3045198 A1 | 7/2016 |

(Continued)

OTHER PUBLICATIONS

International Search Report for PCT/JP2021/013010 dated Jun. 8, 2021.

*Primary Examiner* — Charles S Bushey
(74) *Attorney, Agent, or Firm* — McDonald Hopkins LLC (57) ABSTRACT

In the present disclosure, air passing through the inside of a humidifier is readily humidified. The humidifier includes a water chamber having a first circulation opening and a second circulation opening for allowing air to circulate. An outlet baffle that covers at least part of the second circulation opening from below is provided on an inner surface of a top cover of the water chamber. A third circulation opening is formed by the outlet baffle. The direction in which the third circulation opening opens intersects the direction in which the first circulation opening opens. A baffle protrudes from the inner surface of the top cover. The baffle is located on a straight path between the third circulation opening and the first circulation opening and extends in a direction that intersects the straight path.

14 Claims, 4 Drawing Sheets

(56) References Cited

U.S. PATENT DOCUMENTS

| | | | |
|---|---|---|---|
| 7,616,871 B2 * | 11/2009 | Kramer | A61M 16/109 392/386 |
| 2004/0055597 A1 | 3/2004 | Virr et al. | |
| 2004/0060559 A1 | 4/2004 | Virr et al. | |
| 2010/0154796 A1 | 6/2010 | Smith et al. | |
| 2010/0170510 A1 * | 7/2010 | Pieri | A61M 16/109 128/203.17 |
| 2015/0202402 A1 | 7/2015 | Kat | |
| 2018/0110944 A1 * | 4/2018 | Dai | A61M 16/0006 |
| 2020/0101259 A1 | 4/2020 | Vivian et al. | |

FOREIGN PATENT DOCUMENTS

| | | |
|---|---|---|
| EP | 3508241 A1 | 7/2019 |
| JP | 2000-337670 A | 12/2000 |
| JP | 2004-524087 A | 8/2004 |
| JP | 2004-524088 A | 8/2004 |
| JP | 2009-504278 A | 2/2009 |
| JP | 2018-064972 A | 4/2018 |

* cited by examiner

HUMIDIFIER

CROSS REFERENCE TO RELATED APPLICATION

This is a continuation of International Application No. PCT/JP2021/013010 filed on Mar. 26, 2021 which claims priority from Japanese Patent Application No. 2020-069629 filed on Apr. 8, 2020. The contents of these applications are incorporated herein by reference in their entireties.

BACKGROUND OF THE DISCLOSURE

Field of the Disclosure

The present disclosure relates to humidifiers.

Description of the Related Art

The humidifier described in Patent Document 1 includes a water chamber in which water is stored. An inlet for introducing air from the outside is formed as an opening in an outer wall of the water chamber. In addition, an outlet for discharging air from inside the water chamber is formed as an opening in another outer wall of the water chamber opposite the outer wall having the inlet. The outlet and inlet are disposed at substantially the same height when the water chamber is in use.

A dividing member is disposed inside the water chamber. The dividing member separates the inlet side and outlet side of the water chamber into separate areas. Water inside the water chamber is stored in the area on the outlet side. A through hole for allowing air to circulate from the inlet-side area to the outlet-side area is provided in the dividing member.

Patent Document 1: Japanese Unexamined Patent Application Publication (Translation of PCT Application) No. 2004-524087

BRIEF SUMMARY OF THE DISCLOSURE

In the humidifier described in Patent Document 1, water is stored in the area on the outlet side. Air flowing into the inside of the water chamber is humidified by contacting the water in the area on the outlet side. Therefore, the greater the distance the air travels after passing through the through holes in the dividing member before reaching the outlet, the more satisfactorily the air will be humidified. However, the air flow and the degree of humidification of the air are not specifically focused upon in the humidifier described in Patent Document 1 and there is room for improvement in this area.

In order to solve the above-described problem, an aspect of the present disclosure provides a humidifier that includes a water chamber capable of storing water thereinside and having a first circulation opening and a second circulation opening for allowing air to circulate. The water chamber includes a tank having an opening in an upper portion thereof and a top cover that is spaced away from a bottom surface part of the tank and covers the opening. At least the second circulation opening out of the first circulation opening and the second circulation opening extends between one main surface of the top cover facing into a space inside the tank and another main surface of the top cover located outside the space of the tank. The one main surface of the top cover is provided with a first baffle covering at least part of the second circulation opening and a second baffle located between the first circulation opening and the second circulation opening when the one main surface of the top cover is viewed in plan view. A third circulation opening is formed and a passage connecting the third circulation opening and the second circulation opening to each other is formed by the first baffle and the one main surface of the top cover. A direction in which the third circulation opening opens is different from a direction in which the first circulation opening opens. The second baffle is located on a straight line connecting the third circulation opening and the first circulation opening to each other and extends in a direction that intersects a path along the straight line when the one main surface of the top cover is viewed in plan view.

With the above configuration, air flowing into the water chamber of the humidifier is discharged to outside the water chamber through the first circulation opening, the third circulation opening of the first baffle, and the second circulation opening. The second baffle is disposed on a straight line connecting the first circulation opening and the third circulation opening to each other so as to obstruct the straight line. Therefore, at least some of the air that passes through the first circulation opening bypasses the second baffle in order to reach the third circulation opening. As a result, the circulation path of air between the first circulation opening and the third circulation opening is lengthened and the air is more readily humidified.

Air passing through the inside of a humidifier is readily humidified.

DETAILED DESCRIPTION OF THE DISCLOSURE

A humidifier of a First Embodiment is described below.

First, the overall configuration of a continuous positive airway pressure device (hereinafter, referred to as a "CPAP device") to which the humidifier of this embodiment has been applied is described.

Figure 1:
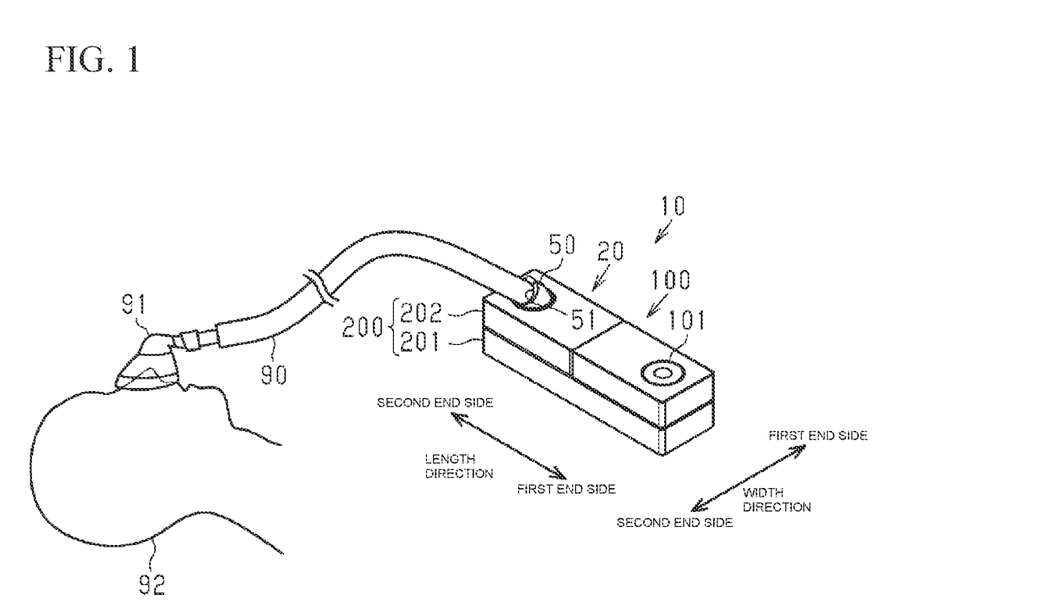
FIG. 1 is a diagram illustrating the state of use of a CPAP device in each embodiment.

As illustrated in FIG. 1, a CPAP device 10 consists of a blower unit 100 and a base unit 200. With the blower unit 100 attached to the base unit 200, the CPAP device 10 has a substantially rectangular parallelepiped shape on the whole. In the following description, when the CPAP device 10 is viewed in plan view, a direction in which long sides extend is referred to as a length direction and a direction in which short sides extend is referred to as a width direction.

The blower unit 100 of the CPAP device 10 has a substantially rectangular parallelepiped shape. Although not illustrated, a passage along which air is circulated and an air-blowing fan that blows the air inside the passage are accommodated inside the blower unit 100. A switch 101 is installed at an upper surface of the blower unit 100. The air-blowing fan inside the blower unit 100 is controlled so as to be turned on/off and so forth by operating the switch 101.

The base unit 200 of the CPAP device 10 is shaped like the letter L when viewed from the side in the width direction. With the blower unit 100 attached to the inner side of the L-shape of the base unit 200, the CPAP device 10 has a substantially rectangular parallelepiped shape, as described above.

An upper outer cover part 202 of the base unit 200 can be removed from a lower base part 201 of the base unit 200. A passage along which air is supplied to the blower unit 100 and a muffler that muffles the sound of air passing along the passage are provided inside the base unit 200. A humidifier 20 that humidifies the air supplied from the blower unit 100 is accommodated inside the base unit 200. The humidifier 20 is described below in more detail.

Figure 2:
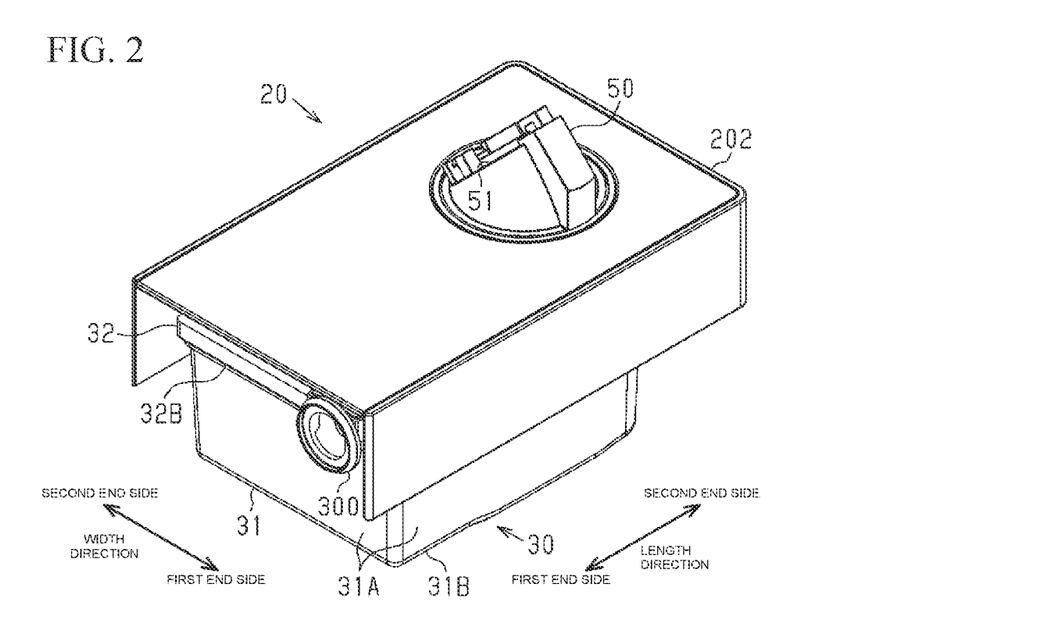
FIG. 2 is a perspective view of a humidifier with an outer cover part attached in a First Embodiment.

As illustrated in FIG. 2, a conduit 50 of the humidifier 20 protrudes from the outer cover part 202 of the base unit 200. As illustrated in FIG. 1, a mask 91 is attached to the conduit 50 via an air tube 90. The mask 91 is attached so as to cover the nose or mouth of a user 92.

With the blower unit 100 attached to the base unit 200, air is supplied to the blower unit 100 through the passage inside the base unit 200. Air blown from the blower unit 100 is then supplied to the humidifier 20 inside the base unit 200 and humidified. The humidified air is then supplied to the mask 91 via the conduit 50 of the humidifier 20 and the air tube 90.

Next, the humidifier 20 is described.

Figure 3:
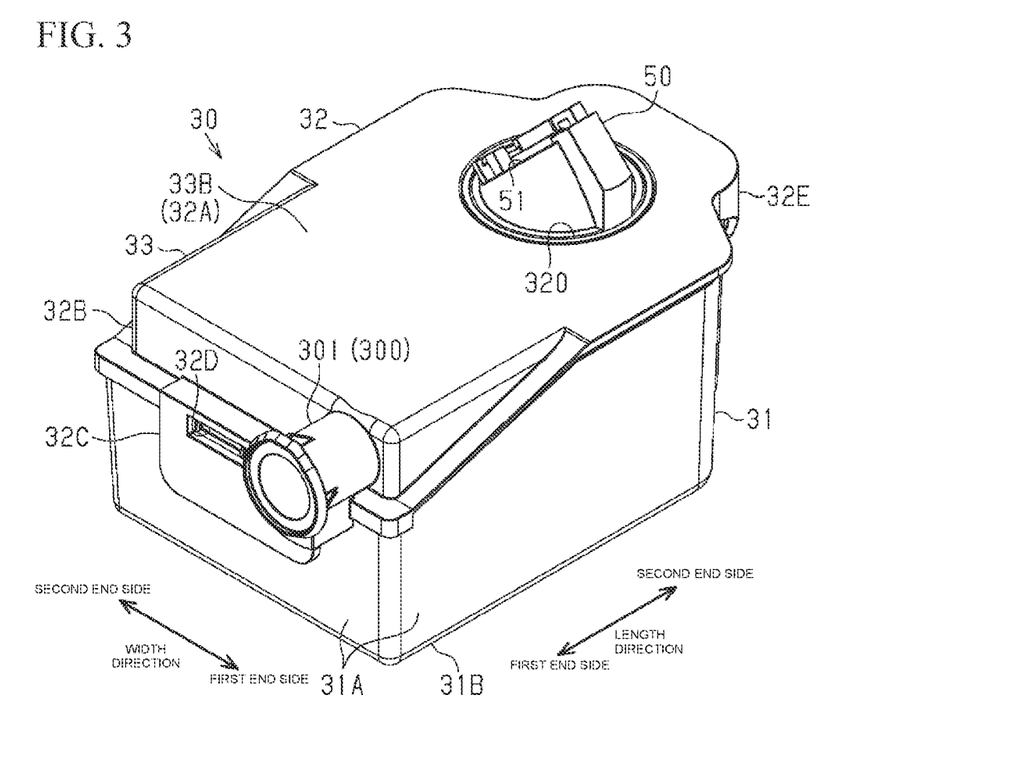
FIG. 3 is a perspective view of the humidifier in the First Embodiment.

As illustrated in FIG. 2, humidifier 20 includes a water chamber 30. The water chamber 30 is substantially rectangular parallelepiped shaped and is hollow inside. As illustrated in FIG. 3, a tank 31 of the water chamber 30 is substantially shaped like a square box on the whole. That is, the tank 31 has four side surface parts 31A and a bottom surface part 31B connected to the lower edges of these side surface parts 31A. A space that is capable of storing water is formed by the four side surface parts 31A and the bottom surface part 31B. An opening of the tank 31 is formed by the upper edges of the side surface parts 31A of the tank 31.

The water chamber 30 has a top cover 32 that is spaced away from the bottom surface part 31B of the tank 31 and covers the opening of the tank 31. The top cover 32 has a top plate 32A that corresponds to the shape of the opening of the tank 31. A side wall 32B extends in an upright manner towards the tank 31 from an edge of the top plate 32A on a first end side in the length direction. The side wall 32B extends up to parts of the edges of the top plate 32A on both sides in the width direction.

Figure 4:
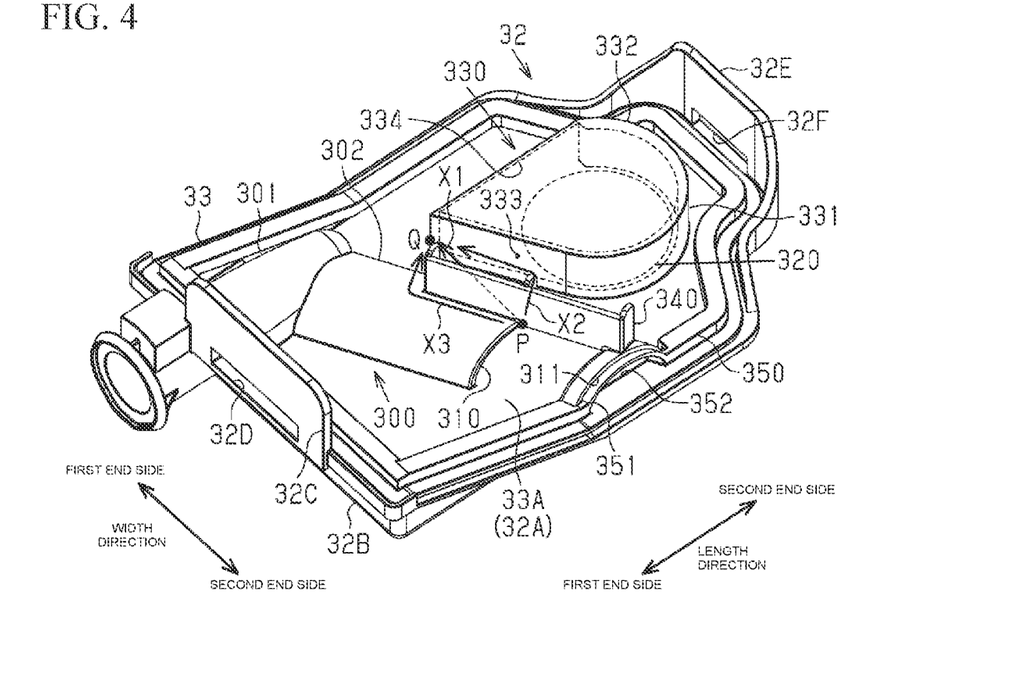
FIG. 4 is a perspective view of an inner surface of a top cover of the humidifier in the First Embodiment.

A plate-shaped first fastening portion 32C extends downward from a lower edge of the side wall 32B. The first fastening portion 32C is disposed at the center of the side wall 32B in the width direction. A through hole 32D extends through the first fastening portion 32C. As illustrated in FIG. 4, a plate-shaped second fastening portion 32E extends downward from an edge of the top cover 32 on a second end side in the length direction. The second fastening portion 32E is disposed at the center, in the width direction, of an edge of the top cover 32 on the second end side in the length direction. A through hole 32F extends through the second fastening portion 32E. When the top cover 32 is attached to the tank 31, the through hole 32D of the first fastening portion 32C and the through hole 32F of the second fastening portion 32E in the top cover 32 engage with protrusions of the tank 31, which are not illustrated. In this way, the top cover 32 is attached to the tank 31.

As illustrated in FIG. 3, a flow tube 300, which is a second tube, extends through the side wall 32B of the top cover 32. The flow tube 300 connects the inside of the water chamber 30 to the outside and is used to supply air into the inside of the water chamber 30.

As illustrated in FIG. 4, the flow tube 300 can be roughly divided into an upstream section 301 extending substantially in the length direction and a downstream section 302 extending in a direction that intersects the direction in which the upstream section 301 extends. In other words, the flow tube 300 extends in a curved manner on the whole. The upstream section 301 is substantially shaped like a circular tube. The upstream section 301 penetrates through the side wall 32B. The upstream section 301 is disposed further towards a first end side in the width direction than the center of the side wall 32B. The downstream section 302 is connected to a downstream end of the upstream section 301. The downstream section 302 is shaped like a semicircular curved plate. Out of the two main surfaces of the top plate 32A, an inner surface 33A is the surface located on the side inside the space of the tank 31 and an outer surface 33B is the surface on the side outside the space, in a state where the top cover 32 is attached to the tank 31. In this embodiment, an air flow path is defined by the curved inner surface of the downstream section 302 and the inner surface 33A of the top cover 32A. The downstream section 302 extends diagonally from a downstream end of the upstream section 301 towards a side of the top cover 32 on a second end side in the width direction. The downstream section 302 extends to an edge of the top cover 32 on the second end side in the width direction.

Figure 6:
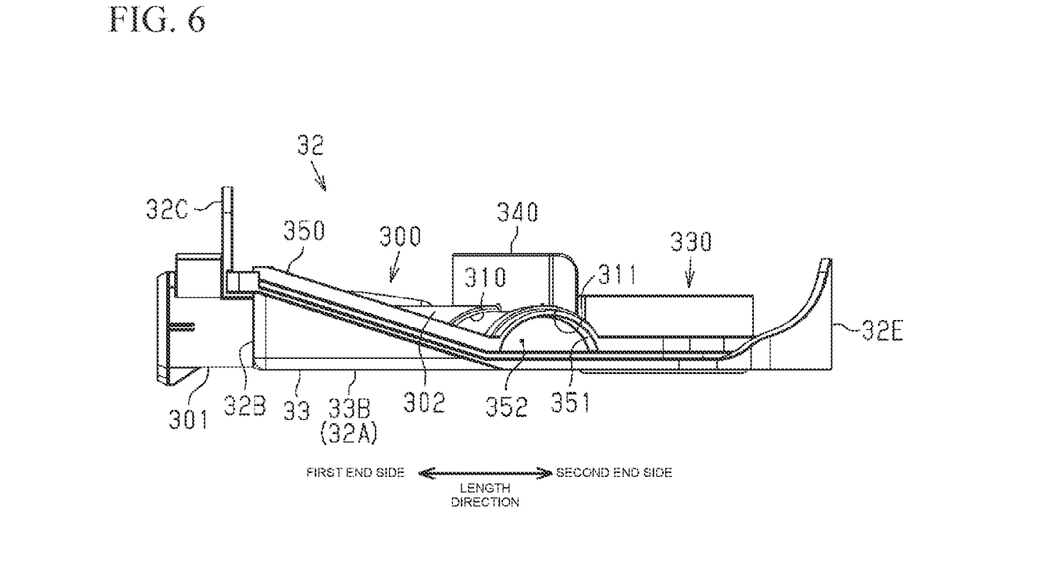
FIG. 6 is a side view of the inner surface of the top cover of the humidifier in the First Embodiment.

As illustrated in FIGS. 4 and 6, an opening 311, which is a fourth circulation opening, is formed at the downstream end of the downstream section 302, i.e., at the leading end of the flow tube 300 on the inner side of the water chamber 30. A first circulation opening 310, which is different from the opening 311, is also formed in the downstream section 302.

Figure 5:
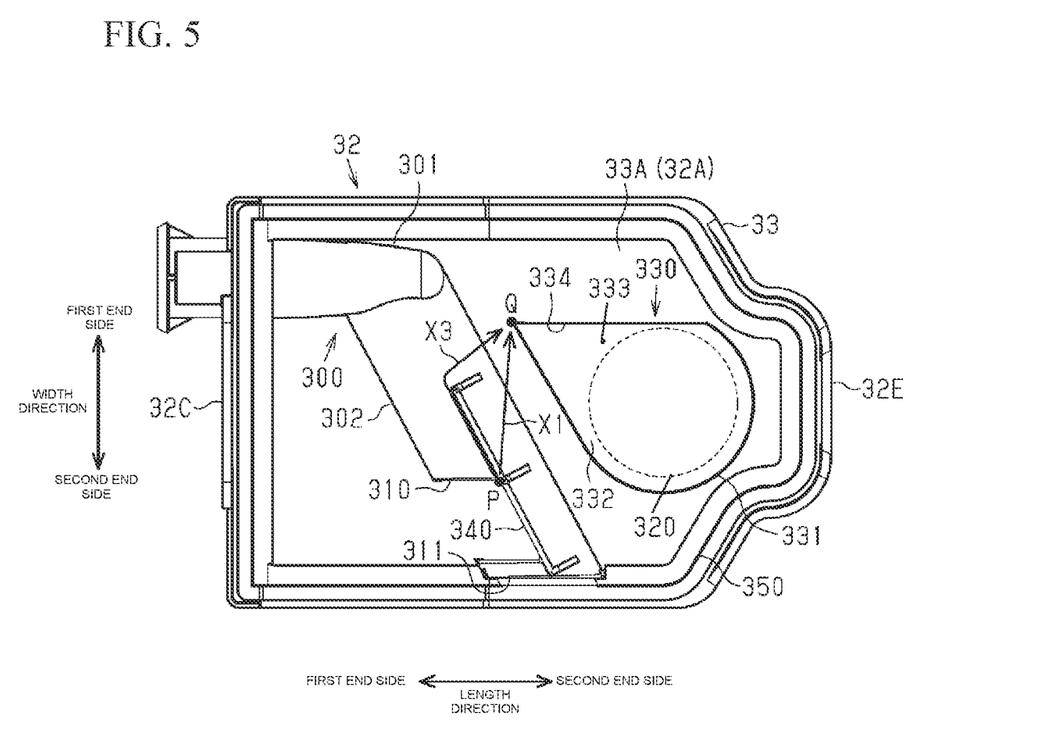
FIG. 5 is a plan view of the inner surface of the top cover of the humidifier in the First Embodiment.

As illustrated in FIGS. 4 and 5, the first circulation opening 310 is disposed downstream of the center of the downstream section 302 in the direction in which the downstream section 302 extends. The first circulation opening 310 is provided on the first end side in the length direction from a central axis line of the downstream section 302. In other words, as illustrated in FIG. 5, when the inner surface 33A of the top plate 32A in the top cover 32 is viewed in plan view, the first circulation opening 310 opens towards a side of the top cover 32 on the first end side in the length direction. In this embodiment, the opening shape of the first circulation opening 310 is a quadrangular shape in plan view.

As illustrated in FIG. 4, in the top cover 32A, a circular second circulation opening 320 extends between the two main surfaces of the top cover 32A, i.e., the inner surface 33A and the outer surface 33B. The second circulation opening 320 is disposed in the top plate 32 so as to be further towards the second end side in the length direction than the flow tube 300. The second circulation opening 320 is disposed substantially at the center in the width direction.

An outlet baffle 330 is provided on the inner surface 33A of the top plate 32A as a first baffle. The outlet baffle 330 covers the second circulation opening 320 from below. The outlet baffle 330 has a side wall 331 standing upright from the inner surface 33A of the top plate 32A. The side wall 331 extends so as to enclose the second circulation opening 320 from three sides, namely, the first end side in the length direction, the second end side in the length direction, and the second end side in the width direction. A baffle plate 332 is connected to a leading end of the side wall 331. The baffle plate 332 is substantially parallel to the inner surface 33A of the top plate 32A. The baffle plate 332 covers the entirety of the second circulation opening 320 when the top cover 32 is viewed in plan view from the side where the inner surface 33A is located.

As mentioned above, the side wall 331 of the outlet baffle 330 is not provided on the first end side in the width direction. Therefore, a third circulation opening 334 is formed by the outlet baffle 330 and the inner surface 33A of the top plate 32A of the top cover 32. This third circulation opening 334 opens towards the first end side in the width direction. An air passage 333, which connects the third circulation opening 334 and the second circulation opening 320 to each other, is formed by the side wall 331 and baffle plate 332 of the outlet baffle 330 and the inner surface 33A of the top plate 32A. The third circulation opening 334 opens at the side of the top cover 32 on the first end side in the width direction, whereas the first circulation opening 310 opens at the side of the top cover 32 on the first end side in the length direction. In other words, the direction in which the first circulation opening 310 opens is different from the direction in which the third circulation opening 334 opens.

As illustrated in FIGS. 4 and 5, a baffle 340, which is a plate-shaped second baffle, protrudes from the downstream section 302 of the flow tube 300 towards the inside of the water chamber 30. The baffle 340 is provided between the first circulation opening 310 and the second circulation opening 320 when the top cover 32 is viewed in plan view from the side where the inner surface 33A is located. Specifically, the baffle 340 is disposed further towards the second end side in the length direction on the top cover 32 than the first circulation opening 310, and extends along an opening edge of the first circulation opening 310. The baffle 340 extends in the axial direction of the downstream section 302 from upstream of the center of the downstream section 302 in the extension direction to the downstream end of the downstream section 302. As illustrated in FIG. 6, a protruding tip of the baffle 340 extending toward the inside of the water chamber 30 is located below the lower end of the opening at the upstream end of the upstream section 301 of the flow tube 300. When water is stored in the water chamber 30 to full capacity, the water surface inside the water chamber 30 is located at the lower end of the opening of the upstream section 301 of the flow tube 300. Therefore, when the water chamber 30 is full, the protruding tip of the baffle 340 is submerged under the water. The position of the water surface when the water chamber 30 is full may be indicated, for example, by a scale on an inner surface of the tank 31.

Here, as illustrated in FIGS. 4 and 5, the shortest distance between the first circulation opening 310 and the third circulation opening 334 of the outlet baffle 330 is represented by the path of an arrow X1 connecting an opening end P of the first circulation opening 310 on a second end side in the length direction and the first end side in the width direction to an opening end Q of the third circulation opening 334 on the first end side in the length direction.

The baffle 340 extends along the opening edge of the first circulation opening 310 on the second end side in the length direction, as described above. In addition, the baffle 340 is disposed further towards the second end side in the length direction than the downstream section 302. Therefore, the baffle 340 is disposed on the shortest path between the first circulation opening 310 and the third circulation opening 334, and extends in a direction intersecting this shortest path.

As illustrated in FIG. 4, a rubber sealing member 350 is attached to the inner surface 33A of the top plate 32A. The sealing member 350 extends along the shape of the outer edge of the top plate 32A. When the top cover 32 is placed over the opening of the tank 31, the top cover 32 and the tank 31 fit together with the inner side of the tank 31 and the outer side of the sealing member 350 contacting each other. This creates a seal between the top cover 32 and the tank 31.

As illustrated in FIGS. 4 and 6, part of the sealing member 350 near the downstream end of the downstream section 302 of the flow tube 300 consists of a curved portion 351, which is downwardly convex. The curved portion 351 follows the curved inner surface of the downstream end of the downstream section 302. A plate-shaped stopper 352 is disposed on the inner side the curved portion 351. The stopper 352 has the same semicircular shape as the opening 311 in plan view. When the sealing member 350 is attached to the top cover 32, the stopper 352 blocks the entire area of the opening 311. The entire sealing member 350 is molded in an integrated manner. The sealing member 350 can be attached to and detached from the inner surface 33A of the top plate 32A. Therefore, when the sealing member 350 is removed from the top plate 32A, the entirety of the opening 311 of the downstream section 302 is open.

As illustrated in FIG. 3, the conduit 50, which is a first tube, extends from the outer surface 33B of the top cover 32 of the water chamber 30. The conduit 50 is connected to the opening edge of the second circulation opening 320, and the inside of the conduit 50 communicates with the second circulation opening 320. The conduit 50 extends diagonally towards the side of the water chamber 30 on the second end side in the width direction. An opening 51 of the conduit 50 on the opposite side from the second circulation opening 320, i.e., the opening 51 on the downstream side, faces towards the side of the water chamber 30 on the second end side in the width direction. In other words, the opening 51 faces towards the opposite side from the third circulation opening 334 with a central axis of the second circulation opening 320 interposed therebetween. The conduit 50 can be rotated with the central axis of the second circulation opening 320 serving as an axis of rotation. The range of rotation of the conduit 50 lies within 90 degrees on both sides of a position on the opposite side of a center axis of the second circulation opening 320 from the third circulation opening 334. In other words, from a state where the conduit 50 faces towards the side of the water chamber 30 on the second end side in the width direction, the conduit 50 can rotate up to 90 degrees towards the side of the water chamber 30 on the first end side in the length direction and towards the side of the water chamber 30 on the second end side in the length direction.

Next, the operation of the First Embodiment is described.

First, the flow of air through the inside of the humidifier 20 when the humidifier 20 is in use is described.

As illustrated in FIGS. 1 and 2, air blown by the blower unit 100 flows into the inside of the water chamber 30 through an opening of the upstream section 301 of the flow tube 300. As illustrated in FIG. 5, air that flows into the flow tube 300 is expelled through the first circulation opening 310 of the downstream section 302 into the space between the top cover 32 and the water surface of the water stored in the tank 31.

The water stored in the tank 31 is heated by a heater or the like, which is not illustrated, disposed on a lower surface of the tank 31. Air having a high humidity accumulates in the vicinity of the water surface of the water inside the tank 31. Therefore, air flowing into the inside of the tank 31 flows and mixes with this high-humidity air near the water surface of the water in the tank 31, which results in the air being humidified.

When the air humidified inside the water chamber 30 reaches the third circulation opening 334 of the outlet baffle 330, the humidified air passes through the air passage 333 defined by the outlet baffle 330 and the inner surface 33A of the top plate 32A of the top cover 32, and reaches the second circulation opening 320. The air passing through the second circulation opening 320 passes through the opening 51 of the conduit 50 and the inside of the air tube 90, and is supplied to the user 92 through the mask 91.

Here, the air discharged from the first circulation opening 310 reaches the third circulation opening 334 of the outlet baffle 330 after passing along various paths inside the water chamber 30. For example, as illustrated in FIG. 4, when air is discharged from the opening end P of the first circulation opening 310 located on the second end side in the length direction and the first end side in the width direction, the air may reach the third circulation opening 334 by flowing along a path that jumps over the baffle 340 from below as indicated by an arrow X2 in the figure. When water is stored in the water chamber 30 to full capacity, the tip of the baffle 340 is in contact with the water surface. Therefore, air discharged from the opening end P is not able to jump over the baffle 340 and pass through as in the path indicated by the arrow X2 in the figure. Therefore, air discharged from the opening end P may reach the third circulation opening 334 along a path that bypasses the baffle 340, as indicated by an arrow X3 in the figure.

Next, a situation in which the humidifier 20 rolls over is described.

As illustrated in FIG. 1, the CPAP device 10 has a substantially rectangular parallelepiped shape that is longer in the length direction than in the width direction and this makes it relatively easy for the CPAP device 10 to roll over in the width direction. Let us suppose that the CPAP device 10 has rolled over so that the side of the CPAP device 10 on the second end side in the width direction is at the bottom.

When the humidifier 20 has rolled over by 90 degrees so that the side of the humidifier 20 on the second end side in the width direction is at the bottom, the third circulation opening 334 of the outlet baffle 330 faces upward. In other words, the second circulation opening 320 is enclosed by the side wall 331 of the outlet baffle 330 except for at the upper side thereof. When the humidifier 20 has rolled over by 90 degrees towards the second end side in the width direction, the opening of the upstream section 301 of the flow tube 300 is disposed on the upper side.

Next, the effects of the First Embodiment are described.

(1-1) In this embodiment, the baffle 340 protrudes from the inner surface 33A of the top plate 32A of the top cover 32. The baffle 340 is located on the shortest path between the third circulation opening 334 of the outlet baffle 330 and the first circulation opening 310, as indicated by the arrow X1 in FIG. 4. The baffle 340 extends in a direction that intersects the shortest path.

Therefore, air discharged from the first circulation opening 310 is blocked by the baffle 340 and cannot reach the third circulation opening 334 by the shortest path. Therefore, the air reaches the third circulation opening 334 by passing along the path indicated by the arrow X2 in FIG. 4, for example, or along the path indicated by the arrow X3 if the water chamber 30 is full of water. These paths are longer than the path indicated by the arrow X1 in the figure, which illustrates the shortest path. Therefore, air discharged into the water chamber 30 is in contact with the water surface inside the water chamber 30 for a longer distance and more readily flows downstream together with humid air. Therefore, the air discharged from the humidifier 20 is more readily humidified.

(1-2) In this embodiment, the first circulation opening 310 opens on the side of the top cover 32 on the first end side in the length direction, and the third circulation opening 334 of the outlet baffle 330 opens on the side of the top cover 32 on the first end side in the width direction. Thus, the direction in which the first circulation opening 310 opens and the direction in which the outlet baffle 330 opens intersect each other, and this facilitates agitation of the air inside the tank 31. Therefore, the length of the flow path of the air circulating inside the water chamber 30 can be lengthened.

(1-3) In this embodiment, the conduit 50, which is connected to the second circulation opening 320, extends from the outer surface 33B of the top plate 32A of the top cover 32. The opening 51 of the conduit faces toward the side of the humidifier 20 on the second end side in the width direction. Therefore, when the CPAP device 10 is used, the CPAP device 10 is often disposed so that the opening 51 of the conduit 50 and the user 92 face each other, as illustrated in FIG. 1. If the user 92 moves while the CPAP device is in this arrangement, it is assumed that the mask 91 and the air tube 90 attached to the user 92 will pull the humidifier 20. In other words, if the CPAP device 10 tips over while the CPAP device 10 is being used, it is expected that the CPAP device 10 will tip over towards the second end side in the width direction.

If the CPAP device 10 were to tip over by 90 degrees such that the side thereof on the second end side in the width direction ends up at the bottom, as described above, the third circulation opening 334 of the outlet baffle 330 would face upward and the opening of the upstream section 301 of the flow tube 300 would be disposed on the upper side. These openings being disposed on the upper side makes it more difficult for water inside the water chamber 30 to reach the second circulation opening 320 or the opening of the upstream section 301 of the flow tube 300. In other words, even if the CPAP device 10 tips over, water is unlikely to leak from the humidifier 20.

(1-4) In this embodiment, the conduit 50 can rotate up to 90 degrees towards the sides of the water chamber 30 on the first end side and the second end side in the length direction from a state where the conduit 50 faces towards the side of the water chamber 30 on the second end side in the width direction. The rotation of the conduit 50 expands the range of movement of the air tube 90, and the humidifier 20 is less likely to tip over even in the case where the user 92 wearing the mask 91 moves. In addition, since the conduit 50 has the above-described range of movement, the opening 51 of the conduit 50 does not face the side of the water chamber 30 on the first end side in the width direction. In other words, it is difficult to use the CPAP device 10 with the air tube 90 extending from the side of the CPAP device 10 on the first end side in the width direction. In this state of use, even if the CPAP device 10 were to roll over, it would be unlikely that the CPAP device 10 would tip over such that the side of the CPAP device 10 on the first end side in the width direction ended up at the bottom. By preventing the CPAP device 10 from rolling over towards the first end side in the width direction, the occurrence of a situation in which water inside the tank 31 flows into the second circulation opening 320 and water leaks from the humidifier 20 can be suppressed.

(1-5) The flow tube 300 is curved, and the direction in which the flow tube 300 extends is different in the upstream section 301 and the downstream section 302. The opening of the flow tube 300 on the upstream side is located near an edge on the first end side in the width direction, whereas the downstream opening 311 of the flow tube 300 is located near an edge on the second end side in the width direction. Therefore, even if the water chamber 30 tips over in the width direction, one out of the upstream opening and the downstream opening 311 of the flow tube 300 is highly likely to be located above the water surface inside the tank 31. Therefore, it is possible to suppress the leakage of the water through the flow tube 300 if the water chamber 30 tips over in the width direction.

(1-6) If a tool is inserted from the opening end of the upstream section 301 in order to clean the inside of the flow tube 300, the tool might not adequately reach the downstream section 302 due to the curvature of the flow tube 300. In this embodiment, the opening 311 is provided at the leading end of the downstream section 302 of the flow tube 300. Therefore, when cleaning the inside of the flow tube 300, a tool can be inserted into the tube from the opening 311 at the leading end of the downstream section 302 of the flow tube 300, and the inside of the flow tube 300 can be easily cleaned.

(1-7) In this embodiment, the sealing member 350 is provided between the inner surface 33A of the top plate 32A of the top cover 32 and the tank 31. The sealing member 350 can be removed from the inner surface 33A of the top cover 32. When cleaning the top cover 32, the sealing member 350 can be removed so as to allow the top cover 32 and the sealing member 350 to be cleaned separately. In addition, the sealing member 350 and the top cover 32 can be dried after being disassembled. This is more hygienic since water is less likely to remain between the two components.

(1-8) In this embodiment, when the sealing member 350 is attached to the inner surface 33A of the top plate 32A of the top cover 32, the curved portion 351 and the stopper 352 block the opening 311 of the downstream section 302 of the flow tube 300. Since the opening 311, which is not needed while the CPAP device 10 is operating, can be closed, the pressure loss of air passing along flow tube 300 can be suppressed.

Next, a humidifier of a Second Embodiment is described. In the following description of the Second Embodiment, the description of the parts that are the same as or similar to those in the First Embodiment is simplified or omitted.

Figure 7:
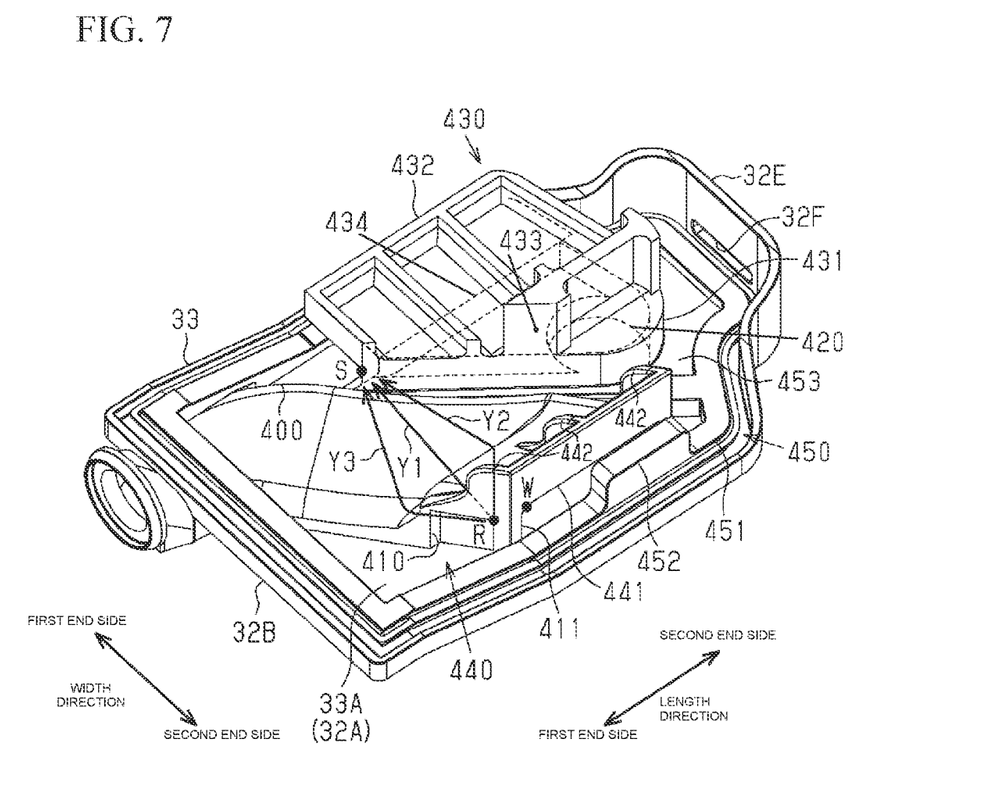
FIG. 7 is a perspective view of an inner surface of a top cover of a humidifier in a Second Embodiment.

As illustrated in FIG. 7, a flow tube 400 extends through the side wall 32B of the top cover 32. The flow tube 400 is shaped like a circular tube outside the water chamber 30 and is shaped like a box that opens towards the inner surface 33A inside the water chamber 30. Therefore, inside the water chamber 30, the air flow path is defined by the box-shaped inner surface of the flow tube 400 and the inner surface 33A of the top cover 32A. When the top cover 32 is viewed in plan view from the side where the inner surface 33A is located, the flow tube 400 extends diagonally from a part of the top cover 32 on the first end side in the length direction and the first end side in the width direction towards a part of the top cover 32 on the second end side in the length direction and the second end side in the width direction. A leading end of the flow tube 400 extends up to the edge of the top cover 32 on the second end side in the width direction. The leading end of the flow tube 400 is located substantially at the center of the top cover 32 in the length direction. The cross-sectional area of the flow path of flow tube 400 gradually increases from the upstream side to the downstream side.

An opening 411 is formed at the downstream end of the flow tube 400, i.e., at the leading end of the flow tube 400 inside the water chamber 30. In addition to the opening 411, a first circulation opening 410 is also formed in the flow tube 400.

The first circulation opening 410 is located downstream from the center of the flow tube 400 in the direction of the extension of the flow tube 400. In this embodiment, the first circulation opening 410 is located near the downstream end of the flow tube 400. The first circulation opening 410 is formed in a side wall of the flow tube 400 on the first end side in the length direction. In other words, when the top cover 32 is viewed in plan view from the side where the inner surface 33A is located, the first circulation opening 410 is formed so as to face in a diagonal direction at a part of the top cover 32 on the first end side in the length direction and the second end side in the width direction. In this embodiment, the opening shape of the first circulation opening 410 is a quadrangular shape in plan view.

A baffle 440 protrudes from the flow tube 400 toward the inside of the water chamber 30. The baffle 440 consists of a plate-shaped main wall 441 and three auxiliary walls 442. The main wall 441 of the baffle 440 extends along the opening edge across the entire opening edge of the downstream end of the flow tube 400. The three auxiliary walls 442 are connected to the main wall 441. The three auxiliary walls 442 are disposed at both sides and at the center of the main wall 441 in the extension direction of the main wall 441. The auxiliary walls 442 extend from the main wall 441 toward the upstream side of the flow tube 400. The auxiliary walls 442 extend though a longer range than the opening range of the first circulation opening 410. In other words, the auxiliary walls 442 are present throughout the entire lower side of the first circulation opening 410. The protruding lengths of the auxiliary walls 442 decrease with increasing proximity to the upstream side of the first circulation opening 410. When water is stored in the water chamber 30 to full capacity, the water surface inside the water chamber 30 is located at the lower end of the flow tube 400 outside the water chamber 30. Therefore, when the water chamber 30 is full, the protruding tip of the main wall 441 and the protruding tips of the auxiliary walls 442 of the baffle 440 are partially immersed in water.

In the top plate 32A, a circular second circulation opening 420 extends between the two main surfaces of the top plate 32A, i.e., the inner surface 33A and the outer surface 33B. The second circulation opening 420 is disposed in the top plate 32A so as to be further towards the second end side in the length direction than the flow tube 400. The second circulation opening 420 is disposed substantially at the center in the width direction.

A rubber sealing member 450 is attached to the inner surface 33A of the top plate 32A. The sealing member 450 has an outer edge portion 451 that extends along the shape of the outer edge of the top plate 32A. In the outer edge portion 451, a protruding portion 452 protrudes towards the inside of the water chamber 30 at a point near the leading end of the flow tube 400. The protruding length of the protruding portion 452 is slightly larger than the vertical dimension of the opening 411. The protruding portion 452 extends from an edge of the opening 411 on the second end side in the length direction towards the first end side in the length direction up to a position approximately halfway across the opening 411. The protruding portion 452 blocks approximately half of the opening 411.

The sealing member 450 has a top plate portion 453 that extends along the inner surface 33A of the top plate 32A. The top plate portion 453 extends in a film-like manner across a part of the top plate 32A located further towards the second end side in the length direction than the flow tube 400. Although not illustrated, an opening extends through the top plate portion 453 so that the top plate portion 453 does not block the second circulation opening. The top plate portion 453 is connected to the outer edge portion 451 at the second end side in the length direction, the first end side in the width direction, and the second end side in the width direction.

A rubber outlet baffle 430 that covers the second circulation opening 420 from below is provided near the second circulation opening 420 in the top plate portion 453. The outlet baffle 430 is integrally molded with the top plate portion 453 of the sealing member 450.

The outlet baffle 430 has a side wall 431 standing upright from the inner surface of the top plate portion 453. The side wall 431 extends so as to enclose the second circulation opening 420 from three sides, namely, the first end side in the length direction, the second end side in the length direction, and the second end side in the width direction. A baffle plate 432 is connected to a leading end of the side wall 431. The baffle plate 432 is substantially parallel to the inner surface 33A of the top plate 32A. Part of the baffle plate 432 on the first end side in the width direction protrudes beyond the range through which the side wall 431 extends. The baffle plate 432 covers the entirety of the second circulation opening 420 when the top cover 32 is viewed in plan view from the side where the inner surface 33A is located. An air passage 433 that is connected to the second circulation opening 420 is defined by the side wall 431 and baffle plate 432 of the outlet baffle 430 and the top plate portion 453 extending along the inner surface 33A of the top cover 32A.

As described above, the side wall 431 of the outlet baffle 430 is not provided on the first end side in the width direction. Therefore, a third circulation opening 434 of the air passage 433 opens towards the first end side in the width direction. The third circulation opening 434 opens at the side of the top cover 32 on the first end side in the width direction, whereas the first circulation opening 410 opens in a diagonal direction at a side of the top cover 32 on the first end side in the length direction and the second end side in the width direction. In other words, the direction in which the first circulation opening 410 opens intersects the direction in which the third circulation opening 434 opens.

Here, as described above, the auxiliary walls 442 are present across the entire area underneath the first circulation opening 410. The auxiliary walls 442 of the baffle 440 are disposed on a straight path indicated by an arrow Y1 connecting an opening end R of the first circulation opening 410 on the second end side in the length direction to an opening end S of the third circulation opening 434 on the first end side in the length direction. In other words, the auxiliary walls 442 of the baffle 440 extend in a direction that intersects the path indicated by the arrow Y1.

The sealing member 450 can be attached to and detached from the inner surface 33A of the top plate 32A. In this embodiment, the sealing member 450 and the outlet baffle 430 are entirely integrally molded with each other. Therefore, when the sealing member 450 is removed from the top plate 32A, the outlet baffle 430 is also removed from the top cover 32. When the sealing member 450 is removed from the top plate 32A, the entirety of the opening 411 at the leading end of the flow tube 400 is open.

Next, the operation of Second Embodiment is described.

As illustrated in FIG. 7, air discharged from the first circulation opening 410 reaches the third circulation opening 434 of the outlet baffle 430 after passing along various paths inside the water chamber 30. For example, as illustrated in FIG. 7, when air is discharged from the opening end R of the first circulation opening 410 on the second end side in the length direction, the air may reach the third circulation opening 434 by flowing along a path that jumps over the auxiliary walls 442 of the baffle 440 from below as indicated by an arrow Y2 in the figure. When water is stored in the water chamber 30 to full capacity, the tips of parts of the auxiliary walls 442 are in contact with the water surface. Therefore, air discharged from the opening end R cannot jump over and pass through the baffle 440 as in the path indicated by the arrow Y2 in the figure. Therefore, air discharged from the opening end R may reach the third circulation opening 434 along a path that bypasses the auxiliary wall 442, as indicated by an arrow Y3 in the figure.

Next, the effects of the Second Embodiment are described. The CPAP device 10 of the Second Embodiment has the following effects in addition to the effect (1-2) of the First Embodiment.

(2-1) In this embodiment, the baffle 440 protrudes from the inner surface 33A of the top plate 32A of the top cover 32 of the water chamber 30. The baffle 440 is located on a straight path connecting the opening end R and the opening end S, as indicated by the arrow Y1 in FIG. 7, out of a straight path connecting the third circulation opening 434 of the outlet baffle 430 and the first circulation opening 410 to each other. The baffle 340 extends in a direction that intersects the straight path indicated by the arrow Y1. Therefore, at least some of the air discharged from the first circulation opening 410 is blocked by the baffle 440 and is unable to reach the third circulation opening 434 by the shortest path. Therefore, the air reaches the third circulation opening 434 by passing along, for example, the path indicated by the arrow Y2 in FIG. 7 or the path indicated by the arrow Y3 if the water chamber 30 is full of water. These paths are longer than the path indicated by the arrow X1 described above. Therefore, air discharged into the water chamber 30 is in contact with the water surface inside the water chamber 30 for a longer distance and more readily flows downstream together with humid air. Therefore, the air discharged from the humidifier 20 is more readily humidified.

(2-2) In this embodiment, the outlet baffle 430 is molded so as to be integrated with the sealing member 450. Therefore, the outlet baffle 430 can be removed from the top cover 32 together with the sealing member 450. When the outlet baffle 430 is removed from the top cover 32 during cleaning the top cover 32, the air passage 433 defined by the side wall 431 of the outlet baffle 430, the baffle plate 432, and the top plate portion 453 is easily visible for cleaning.

(2-3) In the state of use of the CPAP device 10, air also flows into the water chamber 30 through the opening 411 of the flow tube 400. The main wall 441 of the baffle 440 is disposed on a straight path from an opening end W of the opening 411 on the first end side in the length direction to the opening end S of the third circulation opening 334 on the first end side in the length direction. Therefore, air discharged from opening 411 bypasses the main wall 441 of baffle 440 and reaches the third circulation opening 434 of outlet baffle 430 by flowing various flow paths. Paths that reach the third circulation opening 434 by bypassing the main wall 441 of the baffle 440 are longer than the straight path from the opening end W of the opening 411 to the opening end S of the third circulation opening 434. Therefore, the flow path length of air discharged from the opening 411 into the water chamber 30 can be lengthened.

(2-4) When the CPAP device 10 is in use, air is discharged into the inside of the water chamber 30 from the first circulation opening 410 and the opening 411. The air circulation path from the first circulation opening 410 to the third circulation opening 434 and the air circulation path from the opening 411 to the third circulation opening 434 communicate with each other, which allows the air to be more easily agitated inside the water chamber 30. Therefore, the length of the flow path of the air circulating inside the water chamber 30 can be lengthened.

This embodiment and the following modifications can be combined with each other to the extent that they are not technically inconsistent.

In each embodiment, the CPAP device 10 may have any configuration as long as the configuration includes the blower unit 100 and the humidifier 20. The shape of the CPAP device 10 is also not restricted. In addition, as long as it is possible to supply and discharge air to and from the humidifier 20, the present disclosure is not limited to the humidifier 20 of the CPAP device 10.

In each of the embodiments, the humidifier 20 may have any configuration so long as the humidifier 20 includes the water chamber 30. For example, the conduit 50 may be omitted and the air tube 90 may be inserted into the second circulation opening 320. For example, the bottom surface of the water chamber 30 may be provided with a metal heat-transfer member in order to improve the heat conduction from the heater. The shape of the humidifier 20 is also not limited to that described in the above embodiments.

In each embodiment, the configuration of the water chamber 30 is not limited. For example, the tank 31 and the top cover 32 may be molded so as to be integrated with each other such that part of a side surface of the tank 31 is open. The top cover 32 may be attached to the tank 31 using a different configuration, without the top cover 32 being provided with the first fastening portion 32C or the second fastening portion 32E.

In each embodiment, the shape of the flow tube 300 may be modified as appropriate. For example, in the First Embodiment, the upstream section 301 and the downstream section 302 may both be formed in a tubular shape without any boundaries therebetween.

The opening directions of the first circulation openings 310 and 410 are not limited to the examples given in the above embodiments. It is sufficient that the opening direction of the first circulation opening 310 or 410 at least intersects the opening direction of the third circulation opening 334 or 434 of the outlet baffle 330 or 430.

In each embodiment, the shape of the second circulation opening 320 or 420 and the arrangement of the second circulation opening 320 or 420 with respect to the top cover 32 may be changed as appropriate. When changing the arrangement of the second circulation opening 320 or 420 with respect to the top cover 32, it is preferable that the second circulation opening 320 or 420 be disposed near the edge of the top cover 32 on the first end side in the width direction supposing a case where the humidifier 20 rolls over such that the second end side thereof in the width direction ends up at the bottom.

In each of the embodiments, the flow tubes 300 and 400 do not have to be structured as integral parts of the top cover 32. For example, the flow tubes 300 and 400 may be tubular members that penetrate through a side surface of the tank 31. The flow tubes 300 and 400 may be configured so as to allow air to circulate thereinside without contacting the top cover 32 inside the water chamber 30.

In each embodiment, the flow tube 300 or 400 may be omitted and the first circulation opening 310 or 410 may be provided in the top cover 32.

In each of the embodiments, the shape of the outlet baffle 330 or 430 may be changed as appropriate. For example, the outlet baffle 330 or 430 may have a hemispherical shape, and may be shaped to cover at least a portion of the second circulation opening 320 or 420 from below and define an air passage together with the inner surface of the top cover 32.

In each embodiment, a plurality of baffles 340 or 440 may be provided. In this case, the baffles 340 or 440 may be disposed along a straight path between the first circulation opening 310 or 410 and the third circulation opening 334 or 434 and so as to extend in a direction intersecting the straight path.

In each of the embodiments, the full capacity state of the water chamber 30 may be set as appropriate. Even in this case, the protruding tips of the baffles 340 and 440 are preferably submerged in water when the water chamber 30 is full.

The sealing member 350 may cover the entire inner surface 33A of the top plate 32A. Members such as the baffle 340 or 440 may be molded so as to be integrated with the sealing member 350 or 450.

In each embodiment, a plurality of openings 311 or 411 may be provided. Furthermore, the openings 311 or 411 may be omitted.

In each embodiment, the shape of conduit 50 is not limited to that described in the above embodiments. For example, the conduit 50 may be shaped so as to protrude from the outer surface 33B of the top plate 32A of the top cover 32 and be curved partway therealong so as to be parallel to the outer surface 33B of the top plate 32A of the top cover 32.

In each embodiment, the range of rotation of conduit 50 can be changed as appropriate. For example, the conduit 50 may be able to rotate through 360 degrees. The conduit 50 may be unable to rotate. The orientation of the opening of the conduit 50 on the opposite side from the second circulation opening 320 or 420 can also be changed as appropriate.

In the First Embodiment, the stopper 352 of the sealing member 350 may cover only part of the area of the opening 311 rather than the entire area of the opening 311. Furthermore, the stopper 352 itself may be omitted. In the Second Embodiment, the protruding portion 452 may cover the entire area of the opening 411 or may be omitted.

In the First Embodiment, the sealing member 350 can also be omitted. For example, if the top cover 32 of the water chamber 30 is itself formed of a soft material such as rubber, the sealing member 350 may be omitted.

10 . . . CPAP device
20 . . . humidifier
30 . . . water chamber
31 . . . tank
32 . . . top cover
50 . . . conduit
300 . . . flow tube
310 . . . first circulation opening
311 . . . opening
320 . . . second circulation opening
330 . . . outlet baffle
333 . . . air passage 334 . . . third circulation opening
340 . . . baffle
350 . . . sealing member

The invention claimed is:

1. A humidifier comprising:
a water chamber capable of storing water thereinside and having a first circulation opening and a second circulation opening for allowing air to circulate,
wherein the water chamber includes a tank having an opening in an upper portion thereof and a top cover covering the opening as being spaced away from a bottom surface portion of the tank,
at least the second circulation opening out of the first circulation opening and the second circulation opening extends between one main surface of the top cover facing into a space inside the tank and another main surface of the top cover located outside the space of the tank,
the one main surface of the top cover is provided with a first baffle covering at least a part of the second circulation opening and a second baffle located between the first circulation opening and the second circulation opening when the one main surface of the top cover is viewed in plan view,
a third circulation opening is provided and a passage connecting the third circulation opening and the second circulation opening is provided by the first baffle and the one main surface of the top cover,
a direction in which the third circulation opening opens is different from a direction in which the first circulation opening opens, and
the second baffle is located on a straight line connecting the third circulation opening and the first circulation opening to each other and extends in a direction intersecting a path along the straight line when the one main surface of the top cover is viewed in plan view.

2. The humidifier according to claim 1,
wherein a first tube connected to the second circulation opening extends from the other main surface of the top cover, and
an opening of the first tube on an opposite side from the second circulation opening, across a central axis of the second circulation opening, faces in an opposite direction from the third circulation opening when looking in a direction along the central axis.

3. The humidifier according to claim 2,
wherein the first tube is attached to the top cover so as to be able to rotate about the central axis, and
a range of rotation of the first tube lies within 90 degrees on both sides of a position on an opposite side of the central axis from the third circulation opening.

4. The humidifier according to claim 1,
wherein the water chamber is provided with a second tube connecting the inside of the water chamber to the outside, and
the second tube extends in a curved manner.

5. The humidifier according to claim 4,
wherein the first circulation opening is provided in a part of the second tube located inside the water chamber, and
a fourth circulation opening different from the first circulation opening is provided at an end of the second tube inside the water chamber.

6. The humidifier according to claim 5,
wherein a sealing member is provided between the one main surface of the top cover and the tank, and
the sealing member blocks at least a part of the fourth circulation opening of the second tube.

7. The humidifier according to claim 1,
wherein a sealing member is provided between the one main surface of the top cover and the tank, and
the first baffle is molded so as to be integrated with the sealing member.

8. The humidifier according to claim 2,
wherein the water chamber is provided with a second tube connecting the inside of the water chamber to the outside, and
the second tube extends in a curved manner.

9. The humidifier according to claim 3,
wherein the water chamber is provided with a second tube connecting the inside of the water chamber to the outside, and
the second tube extends in a curved manner.

10. The humidifier according to claim 2,
wherein a sealing member is provided between the one main surface of the top cover and the tank, and
the first baffle is molded so as to be integrated with the sealing member.

11. The humidifier according to claim 3,
wherein a sealing member is provided between the one main surface of the top cover and the tank, and
the first baffle is molded so as to be integrated with the sealing member.

12. The humidifier according to claim 4,
wherein a sealing member is provided between the one main surface of the top cover and the tank, and
the first baffle is molded so as to be integrated with the sealing member.

13. The humidifier according to claim 5,
wherein a sealing member is provided between the one main surface of the top cover and the tank, and
the first baffle is molded so as to be integrated with the sealing member.

14. The humidifier according to claim 6,
wherein a sealing member is provided between the one main surface of the top cover and the tank, and
the first baffle is molded so as to be integrated with the sealing member.

* * * * *